United States Patent [19]

Richter et al.

[11] 4,215,220

[45] Jul. 29, 1980

[54] 1-(2-OXYSUBSTITUTED-3-ANILINO-PROPYL)-IMIDAZOLES

[75] Inventors: Carl Richter; Georg Feth, both of Schaffhausen, Switzerland

[73] Assignee: Cilag-Chemie A.G., Schaffhausen, Switzerland

[21] Appl. No.: 940,911

[22] Filed: Sep. 11, 1978

[51] Int. Cl.$^2$ .......................................... C07D 233/60
[52] U.S. Cl. .................. 548/341; 424/273 R
[58] Field of Search .................................. 548/341

[56] References Cited

U.S. PATENT DOCUMENTS

| | | | |
|---|---|---|---|
| 3,575,999 | 4/1971 | Godefroi et al. | 548/336 |
| 3,658,813 | 4/1972 | Godefroi et al. | 548/341 |
| 3,717,655 | 2/1973 | Godefroi et al. | 548/341 |
| 3,793,453 | 2/1974 | Godefroi et al. | 424/273 R |
| 3,796,704 | 3/1974 | Metzger et al. | 548/341 |
| 3,839,574 | 10/1974 | Godefroi et al. | 424/273 R |
| 3,927,017 | 12/1975 | Heerej et al. | 424/273 R |
| 4,036,970 | 7/1977 | Walker et al. | 424/273 R |
| 4,036,973 | 7/1977 | Walker et al. | 548/341 |

Primary Examiner—Natalie Trousof
Attorney, Agent, or Firm—Benjamin F. Lambert

[57] ABSTRACT

Compounds of the class of 1-(3-anilinopropyl)-imidazoles oxysubstituted in the 2-position having antimicrobial activity.

22 Claims, No Drawings

1-(2-OXYSUBSTITUTED-3-ANILINOPROPYL)-IMIDAZOLES

BACKGROUND OF THE INVENTION

A number of antibacterial and antifungal imidazoles are described in the following United States patents:
U.S. Pat. No. 3,575,999;
U.S. Pat. No. 3,658,813;
U.S. Pat. No. 3,717,655;
U.S. Pat. No. 3,793,453;
U.S. Pat. No. 3,839,574; and
U.S. Pat. No. 3,927,017.

The compounds of the present invention differ from such prior art compounds by having an oxy function in the 2-position and an anilino function in the 3-position of the N-propyl substituent on the imidazole ring.

DESCRIPTION OF THE PREFERRED EMBODIMENTS

This invention relates to a novel class of imidazole derivatives and more particularly to 1-(2-oxysubstituted-3-anilinopropyl)-imidazoles having the formula:

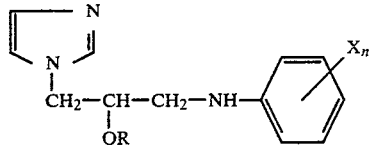

wherein n is an integer from zero to 3, X is halo, and R is a member selected from the group consisting of loweralkyl, benzyl, mono-, di- and tri-halobenzyl, and

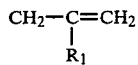

in which $R_1$ is H or halo.

The term "loweralkyl" as used herein is meant to include straight and branch chained aliphatic hydrocarbon radicals containing from 1 to about 6 carbons, such as, for example, methyl, ethyl, propyl, isopropyl, butyl, isobutyl, tert-butyl, pentyl, hexyl and the like; and the term "halo" is generic to halogens of atomic weight less than 127, i.e., chloro, bromo, fluoro and iodo, with chloro being most preferred.

The therapeutically active acid addition salts of the foregoing compounds (I) are also embraced within the scope of this invention.

The preferred compounds of formula (I) are those having the formula:

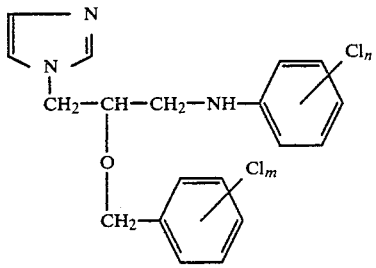

wherein n is as previously described and m is the integer 1 or 2. The most preferred compounds are those of formula (I-a) wherein at least one of said n and m is 2.

The compounds of formula (I) are conveniently prepared by N-alkylation of imidazole (II), which is previously converted into the form of an alkali metal salt, preferably sodium, such as, for example, by treatment with an alkali metal alkoxide, e.g., sodium methoxide, with an appropriate 2-hydroxy-3-anilinopropyl halide, preferably the chloride (III), wherein X and n are as previously defined, to yield the 1-(2-(hydroxy-3-anilinopropyl)-imidazoles of formula (IV).

The reaction is suitably carried out in an appropriate polar organic solvent such as, for example, dimethylformamide (DMF) dimethylacetamide, benzonitrile, higher boiling alcohols such as butanol, and the like.

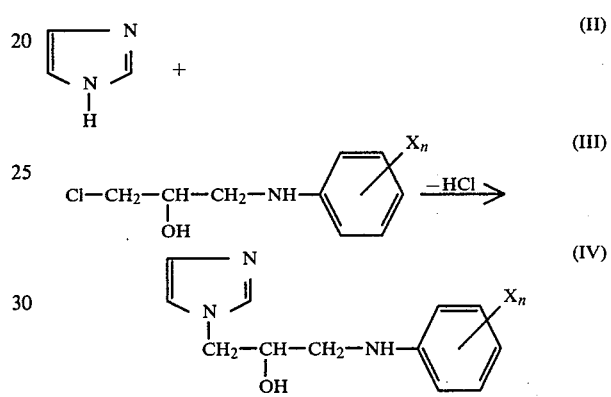

The 1-(2-hydroxy-3-anilinopropyl)-imidazoles of formula (IV), which are useful precursors for making the 2-oxysubstituted compounds of formula (I), are deemed to be novel compounds and, as such, they constitute an additional feature of this invention. The 2-hydroxy function of (IV) is first converted into its corresponding alkali metal salt, for example, by treatment with sodium amide, sodium or lithium hydride, and the like, and the thus-obtained salt (V), wherein M stands for alkali metal, is condensed with an appropriate halide of formula (VI), preferably the chloride, wherein R is as previously described, to yield the 2-oxysubstituted compounds of formula (I). Suitable solvents for the condensation reaction include aromatic hydrocarbons, e.g., benzene, toluene, xylene and the like, dimethylformamide, ethers, e.g., tetrahydrofuran, dioxane and the like, etc. In order to enhance the rate of the reaction, the use of somewhat elevated temperatures is appropriate and most conveniently the reaction is carried out at the reflux temperature of the reaction mixture. The foregoing reaction scheme is illustrated as follows:

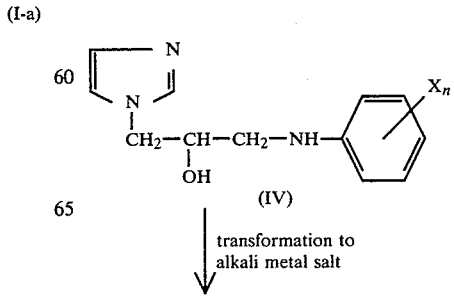

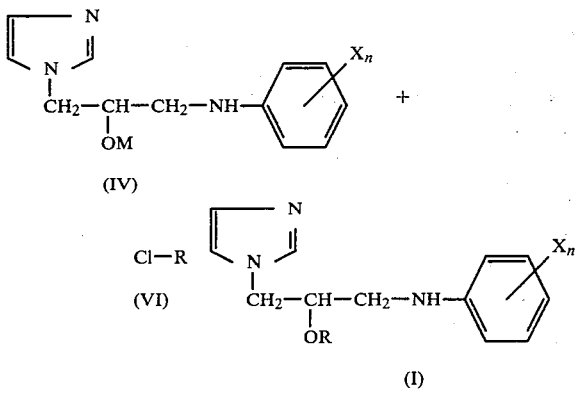

(IV)

(VI) Cl—R (I)

The imidazole derivatives of formula (I), because they crystalize considerably easier as salts, are conveniently recovered from the reaction mixture in the form of an acid addition salt, e.g., as the hydrochloride, nitrate, phosphate, methanesulfonate, etc. by treatment of the base with a suitable acid. In particular, oxalic acid salts readily crystallize from water, ketones and alcohols. They are thus especially useful in the isolation, purification and identification of compounds (I). The thus-obtained salts are converted to the free base form in the usual manner, e.g., by reaction with alkali such as sodium or potassium hydroxide.

The compounds (I) in base form may be converted to pharmaceutically acceptable acid addition salts by reaction with an appropriate acid, such as, for example, an inorganic acid such as hydrohalic acid, i.e., hydrochloric, hydrobromic or hydroiodic acid; sulfuric, nitric or thiocyanic acid; a phosphoric acid; an organic acid such as acetic, propionic, glycolic, lactic, pyruvic, oxalic, malonic, succinic, maleic, fumaric, malic, tartaric, citric, benzoic, cinnamic, mandelic, methanesulfonic, ethanesulfonic, hydroxyethanesulfonic, p-toluenesulfonic, salicyclic, p-aminosalicyclic, 2-phenoxybenzoic, 2-acetoxybenzoic acid and the like.

Due to the presence of an asymmetric carbon in the subject compounds (I), it is evident that their existence in the form of stereochemical optical isomers (enantiomorphs) is possible. If desired, the resolution and isolation or the production of a particular form can be accomplished by application of the general principles known in the art. Said enantiomers are naturally intended to be included within the scope of this invention.

The precursors of formula (III) are generally known in the literature and can be readily obtained by the reaction of aniline or an appropriately substituted aniline with epichlorohydrin in a suitable organic solvent, for example, ethanol acidified with HCl.

The compounds of formula (I) and acid addition salts thereof are effective antimicrobial agents which are particularly useful in combatting fungi and bacteria as demonstrated by their broad spectrum of anti-fungal and anti-bacterial action. Typical of the microorganisms susceptible to the antimicrobial activity of the subject compounds are the following:

1. *Staphylococcus aureus*
2. *Streptococcus pyogenes*
3. *Candida alibcans*
4. *Candida tropicalis*
5. *Cryptococcus neoformans*
6. *Trichophyton rubrum*
7. *Trichophyton mentagrophytes*
8. *Microsporum canis*
9. *Phialophore verrucosa*

The subject compounds (I) and acid addition salts thereof may be employed as antimicrobial agents and formulated into useable compositions by the same methods taught in the aforementioned prior art patents. When the subject compounds are employed in combination with suitable carriers, e.g., in solution, suspension, dust, powder, cream, emulsion, aerosol and the like forms, a high activity over a very high range of dilution is observed. For example, concentrations of the active ingredient ranging from 0.1–10 percent by weight, based on the weight of composition employed, are found effective in combatting fungi or bacteria. Of course, higher concentrations may also be employed as warranted by the particular situation.

The subject compounds and compositions thereof can be applied by conventional methods. For example, a fungus or bacterial growth or a material to be treated or to be protected against attack by fungus or bacterium can be treated with the subject compounds and the compositions thereof by dusting, sprinkling, spraying, brushing, dipping, smearing, impregnating or other suitable means.

Typical examples of the formula (I) compounds that may be prepared by use of appropriate starting materials are:

1-[2-(4-bromobenzyloxy)-3-(2,4-dichloroanilino)-propyl]-imidazole;

1-[3-anilino-2-(2,4-dibromobenzyloxy)-propyl]-imidazole;

1-[3-(3,4-dibromoanilino)-2-(2,4-dibromobenzyloxy)-propyl]-imidazole; and

1-[3-(2,3-dibromoanilino)-2-(4-chlorobenzyloxy)-propyl]-imidazole.

The following examples are intended to illustrate, but not to limit, the scope of the present invention. Unless otherwise stated, all parts are by weight.

EXAMPLE I

1-[2-(4-Chlorobenzyloxy)-3-(2,4-dichloroanilino)-propyl]-imidazole

A. 324.0 Grams (2.0 mol) of 2,4-dichloroaniline, 400 ml absolute ethanol, 185.1 g (2.0 mol) of epichlorohydrin and 3 g of conc. hydrochloric acid are added together in this sequence with stirring and then allowed to stand for 12 days. The solution is thereafter concentrated in vacuum to a brown oily residue which is distilled in high vacuum. The main fraction, which boils between 130° C. and 153° C./0.01 Torr, is collected and redistilled, yielding 209 g of N-(3-chloro-2-hydroxypropyl)-2,4-dichloroaniline as a clear liquid, boiling at 142°–145° C./0.01 Torr.

B. 108 Grams (1.586 mol) of imidazole and 283 g (1.574 mol) of sodiummethylate solution 30% in methanol are mixed and the solution is then concentrated to dryness under reduced pressure at 50° C. The crystalline residue is dissolved in 400 ml dimethylformamide at 110° C. A solution of 259 g (1.017 mol) of N-(3-chloro-2-hydroxypropyl)-2,4-dichloroaniline in 500 ml of dimethylformamide is added dropwise at 110° C. within 30 minutes. Upon completion the reaction mixture is refluxed for 2 hours and then cooled down. The solution is now added dropwise to 3400 ml of water at room temperature within 30 minutes and stirred for another hour. The precipitated granular substance is filtered off, washed with water and dried in vacuum at 50° C. to yield 263.5 g 1-[3-(2,4-dichloroanilino)-2-hydroxypropyl]-imidazole, M.P. 107°–109° C.

C. To a stirred mixture of 3.3 g (0.137 mol) of sodium hydride in 150 ml of tetrahydrofuran, 34.5 g (0.12 mol) of 1-[3-(2,4-dichloroanilino)-2-hydroxypropyl]-imidazole are added at room temperature. The reaction mixture is stirred for another hour at room temperature until the intense formation of hydrogen decreases. The solution is heated to reflux temperature within half an hour and this temperature is maintained for 4 hours. After the crystal paste has cooled down, 16.5 g (0.102 mol) of 4-chlorobenzyl chloride are added and the reaction mixture is heated and refluxed for 4 hours. After cooling 30 ml of water are added dropwise in a nitrogen atmosphere, whereby the surplus sodium hydride is destroyed. The mixture is stirred for another hour at room temperature and then concentrated under reduced pressure at 40° C. The oily brown residue is mixed with 250 ml of toluene and 150 ml of water and shaken thoroughly. The toluene phase is separated, twice washed with 250 ml of water each, dried over sodium sulfate and filtered thereafter. After concentration under reduced pressure at 50° C., 45 g of a viscous oil is obtained. To this oil 250 ml of water and 10 g of oxalic acid are added, the mixture then briefly heated to the boiling point and cooled down to room temperature. The crystallized oxalate salt is filtered off, washed with water and dried at 50° C. in a vacuum dryer. The raw product is recrystallized from 200 ml of ethanol. There is thus obtained 37 g of 1-[2-(4-chlorobenzyloxy)-3-(2,4-dichloroanilino)-propyl]-imidazole oxalate, M.P. 141°–2° C.

D. The free base is obtained by suspending 20 g (0.04 mol) of the oxalate salt in 100 ml of water at 50° C. and adding 5 g (0.089 mol) potassium hydroxide. The precipitated viscous oil is dissolved by adding 120 ml of toluene at 50° C. The organic phase is separated, washed twice with water and dried over potassium carbonate. Then the toluene solution is concentrated under reduced pressure to one third of the initial volume. The crystals already precipitated are again dissolved by heating up to 80° C.; the solution is then left standing overnight. The crystal mass is filtered off, washed with toluene and dried under vacuum at 60° C./12 Torr to yield 13.6 g of 1-[2-(4-chlorobenzyloxy)-3-(2,4-dichloroanilino)-propyl]-imidazole, M.P. 93°–95° C.

E. The nitrate salt can be obtained in the following way: 20 g (0.48 mol) of the above base are dissolved in 50 ml of methanol. 4.8 Grams of conc. nitric acid diluted with 20 ml of water are added dropwise to the methanolic solution. There precipitates an oil that crystallizes after some time. The reaction mixture is allowed to stand for 24 hours. The resultant crystal mass is then filtered off, washed with water and dried in vacuum at 50° C. to yield 21 g of 1-[2-(4-chlorobenzyloxy)-3(2,4-dichloroanilino)-propyl]-imidazole nitrate, M.P. 105°–107° C.

EXAMPLE 2

1-[2-(4-Chlorobenzyloxy)-3-(3,4-dichloroanilino)-propyl]-imidazole

A. 24.3 Grams (0.15 mol) of 3,4-dichloroanilino, 30 ml of absolute ethanol, 13.9 g (0.15 mol) of epichlorohydrin and 0.3 g conc. hydrochloric acid are added together in this sequence with stirring. The mixture is then left standing at room temperature for 6 days and subsequently concentrated under vacuum at 40°/12 Torr. The oily residue is absorbed in 75 ml of cyclohexane, mixed with a few seed crystals and stirred until complete crystallization is obtained. The mixture is allowed to stand overnight. The crystallization product is then successively filtered off, washed with 30 ml of cyclohexane, recrystallized from 300 ml of cyclohexane, filtered off and dried under reduced pressure at 40° C./12 Torr to yield 18.4 g of N-(3-chloro-2-hydroxypropyl)-3,4-dichloroaniline, M.P. 51°–53° C.

B. 19.9 Grams (0.293 mol) of imidazole and 54.7 g (0.304 mol) of sodium methylate solution (30% in methanol) are mixed and concentrated to dryness at 50° C./12 Torr. 80 Ml of dimethylformamide are added to the thus-formed imidazole sodium salt. The mixture is heated to 110° C. and a solution of 50 g (0.197 mol) of N-(3-chloro-2-hydroxypropyl)-3,4-dichloroaniline in 100 ml of dimethylformamide is added dropwise at this temperature over a period of 30 minutes. This addition finished, the reaction solution is further heated and refluxed for 2 hours. The solution is then cooled to 90° C. and 650 ml of water are added. The reaction mixture is left standing for 12 hours. The solid precipitant is filtered off, washed with water and dried at 50° C./12 Torr. For purification the substance is recrystallized under filtration with active charcoal from 100 ml ethyl acetate to yield 22 g of 1-[3-(3,4-dichloroanilino)-2-hydroxypropyl]-imidazole, M.P. 98°–100° C.

C. To 400 ml of tetrahydrofuran 8.8 g (0.366 mol) of sodium hydride followed by 92 g (0.320 mol) of 1-[3-(3,4-dichloroanilino)-2-hydroxypropyl]imidazole are added with stirring at room temperature. The formation of hydrogen stops after 1 hour and the reaction mixture is heated and refluxed for 5 hours. After cooling, 44 g (0.273 mol) of 4-chlorobenzylchloride are added. The solution is again heated to boiling temperature and refluxed for 4 hours. After cooling, 10 ml of water are added dropwise under nitrogen and the crystal cake is concentrated at 50° C./12 Torr. The residue is dissolved in 1500 ml of toluene and the solution washed twice with 300 ml of water each, filtered and concentrated to one third of its original volume under reduced pressure. The crystallized product is filtered off, washed with 100 ml of toluene in portions and dried in vacuum at 50° C./12 Torr. The raw substance is recrystallized under filtration with charcoal in a mixture of 300 ml of ethanol and 100 ml of water, filtered off and dried in vacuum at 50° C./12 Torr to yield 55.3 g of 1-[2-(4-chlorobenzyloxy)-3-(3,4-dichloroanilino)-propyl]-imidazole, M.P. 102.5°–103° C.

D. 10.2 Grams (0.025 mol) of the above base and 2.45 g (0.025 mol) of phosphoric acid are dissolved in 120 ml of water at boiling temperature and the mixture then cooled. The crystallized substance is filtered off and dried in vacuum at 50° C./12 Torr. There is obtained 12.4 g 1-[2-(4-chlorobenzyloxy)-2-(3,4-dichloroanilino)-propyl]-imidazol phosphate, M.P. 153°–154° C.

E. 5.13 Grams (0.0125 mol) of the base are dissolved in 50 ml of acetone at room temperature. 1.2 Grams (0.0125 mol) of methanesulfonic acid dissolved in 10 ml of acetone are added and the solution is left standing for 12 hours. The precipitated crystals are filtered off and dried in vacuum at 50° C./12 Torr to yield 6.1 g 1-[2-(4-chlorobenzyloxy)-3-(3,4-dichloroanilino)-propyl]-imidazole methanesulfonate, M.P. 135°–136° C.

EXAMPLE 3

By following the procedures of Examples 1 and 2, except that an equivalent amount of appropriate starting materials are employed, the following compounds of formula (I) are obtained:

A. From imidazole and N-(3-chloro-2-hydroxypropyl)-aniline [J.Org.Chem. 25, 1428 (1960)], is obtained 1-(3-anilino-2-hydroxypropyl)-imidazole, M.P. 108°–109° C., which is in turn reacted with 2,4-dichlorobenzylchloride to yield 1-[3-anilino-2-(2,4-dichlorobenzyloxy)-propyl]-imidazole; M.P. of oxalate salt is 121°–123° C.

B. Reaction of imidazole and N-(3-chloro-2-hydroxypropyl)-4-chloroaniline [Current Sci. (India) 4, 142-4 (1959)] yields 1-[3-(4-chloroanilino)-2-hydroxypropyl]-imidazole, M.P. 123°–125° C., which is in turn reacted with 2,4-dichlorobenzyl chloride to yield 1-[3-(4-chloroanilino)-2-(2,4-dichlorobenzyloxy)-propyl]-imidazole; M.P. of oxalate salt is 134°–135° C.; M.P. of hydrochloride salt is 161°–163° C.

C. Reaction of 1-[3-(2,4-dichloroanilino)-2-hydroxypropyl]-imidazole with 3-chlorobenzyl bromide yields 1-[2-(3-chlorobenzyloxy)-3-(2,4-dichloroanilino)-propyl]-imidazole; M.P. of oxalate salt is 118°–119° C.

D. Reaction of 1-[3-(2,4-dichloroanilino)-2-hydroxypropyl]-imidazole with 2-chlorobenzyl chloride yields 1-[2-(2-chlorobenzyloxy)-3-(2,4-dichloroanilino)-propyl]-imidazole; M.P. of oxalate salt is 137°–139° C.; M.P. of hydrochloride salt is 139°–140° C.

E. Reaction of 1-[3-(2,4-dichloroanilino)-2-hydroxypropyl]-imidazole with allyl chloride yields 1-[2-allyloxy-3-(2,4-dichloroanilino)-propyl]-imidazole; M.P. of oxalate salt is 124°–125° C.

F. Reaction of 1-[3-(2,4-dichloroanilino)-2-hydroxypropyl]imidazole with 2,3-dichloro-1-propene yields 1-[2-(2-chloropropene-(2)-yl-oxy)-3-(2,4-dichloroanilino)-propyl]-imidazole; M.P. of oxalate salt is 107°–110° C.

G. Reaction of 1-[3-(3,4-dichloroanilino)-2-hydroxypropyl]-imidazole with 2,4-dichlorobenzyl chloride yields 1-[3-(3,4-dichloroanilino)-2-(2,4-dichlorobenzyloxy)propyl]-imidazole. The base, purified by recrystallization from isopropanol, melts at 116°–117° C.; the methanesulfonate salt melts at 141°–143° C.

H. Reaction of 1-[3-(3,4-dichloroanilino)-2-hydroxypropyl]-imidazole with n-butyl bromide yields 1-(2-butyloxy-3-(3,4-dichloroanilino)-propyl]-imidazole; M.P. of oxalate salt is 111°–112° C.

I. Reaction of 2,4,5-trichloroaniline with eipichlorohydrin yields N-(3-chloro-2-hydroxypropyl)-2,4,5-trichloroaniline, an oily liquid boiling at 166°–167° C./0.04 Torr. Reaction of the latter intermediate with imidazole yields 1-[3-(2,4,5-trichloroanilino)-2-hydroxypropyl]-imidazole, M.P. 156°–158° C., which is in turn reacted with p-chlorobenzyl chloride to yield 1-[2-(4-chlorobenzyloxy)-3-(2,4,5-trichloroanilino)-propyl]-imidazole; M.P. of oxalate salt is 160°–162° C.; M.P. of methanesulfonate salt is 114°–116° C.

J. Reaction of 1-[3-(3,4-dichloroanilino)-2-hydroxypropyl]-imidazole with 2,4-dibromobenzyl chloride yields 1-[2-(2,4-dibromobenzyloxy)-3-(3,4-dichloroanilino)-propyl]-imidazole.

K. Reaction of 1-[3-(2,4,5-trichloroanilino)-2-hydroxypropyl]-imidazole with p-bromobenzyl chloride yields 1-[2-(4-bromobenzyloxy)-3-(2,4,5-trichloroanilino)-propyl]-imidazole.

What is claimed is:

1. A compound selected from the group consisting of a 1-(2-oxysubstituted-3-anilinopropyl)-imidazole having the formula:

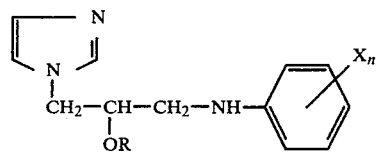

and the therapeutically active acid addition salts thereof wherein n is an integer from zero to 3, X is halo and R is a member selected from the group consisting of loweralkyl, benzyl, mono-, di- and trihalobenzyl, and

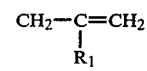

in which $R_1$ is a member selected from the group consisting of hydrogen and halo.

2. A compound selected from the group consisting of a 1-(2-oxysubstituted-3-anilinopropyl)-imidazole having the formula:

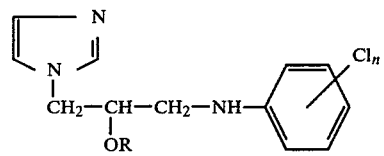

and the therapeutically active acid addition salts thereof wherein n is an integer from zero to 3 and R is a member selected from the group consisting of loweralkyl, benzyl, mono-, di- and trichlorobenzyl, and

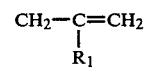

in which $R_1$ is a member selected from the group consisting of hydrogen and chloro.

3. A compound selected from the group consisting of a 1-(2-oxysubstituted-3-anilinopropyl)-imidazole having the formula:

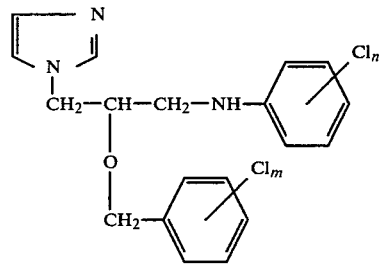

and the therapeutically active acid addition salts thereof wherein n is an integer from zero to 3 and m is the integer 1 or 2.

4. The compounds of claim 3 where at least one of said n and m is 2.

5. A compound selected from the group consisting of 1-[2-(4-chlorobenzyloxy)-3-(2,4-dichloroanilino)- propyl]-imidazole and the therapeutically active acid addition salts thereof.

6. A compound selected from the group consisting of 1-[2-(4-chlorobenzyloxy)-3-(3,4-dichloroanilino)-propyl]-imidazole and the therapeutically active acid addition salts thereof.

7. A compound selected from the group consisting of 1-[3-anilino-2-(2,4-dichlorobenzyloxy)-propyl]-imidazole and the therapeutically active acid addition salts thereof.

8. A compound selected from the group consisting of 1-[3-(4-chloroanilino)-2-(2,4-dichlorobenzyloxy)-propyl]-imidazole and the therapeutically active acid addition salts thereof.

9. A compound selected from the group consisting of 1-[2-(3-chlorobenzyloxy)-3-(2,4-dichloroanilino)-propyl]-imidazole and the therapeutically active acid addition salts thereof.

10. A compound selected from the group consisting of 1-[2-(2-chlorobenzyloxy)-3-(2,4-dichloroanilino)-propyl]-imidazole and the therapeutically active acid addition salts thereof.

11. A compound selected from the group consisting of 1-[2-allyloxy-3-(2,4-dichloroanilino)-propyl]-imidazole and the therapeutically active acid addition salts thereof.

12. A compound selected from the group consisting of 1-[2-(2-chloropropene-(2)-yl-oxy)-3-(2,4-dichloroanilino)-propyl]-imidazole and the therapeutically active acid addition salts thereof.

13. A compound selected from the group consisting of 1-[3-(3,4-dichloroanilino)-2-(2,4-dichlorobenzyloxy)-propyl]-imidazole and the therapeutically active acid addition salts thereof.

14. A compound selected from the group consisting of 1-[2-butyloxy-3-(3,4-dichloroanilino)-propyl]-imidazole and the therapeutically active acid addition salts thereof.

15. A compound selected from the group consisting of 1-[2-(4-chlorobenzyloxy)-3-(2,4,5-trichloroanilino)-propyl]-imidazole and the therapeutically active acid addition salts thereof.

16. A compound selected from the group consisting of 1-(2-hydroxy-3-anilinopropyl)-imidazole having the formula:

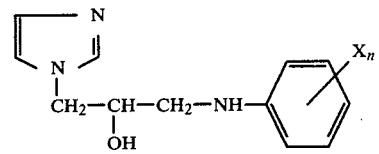

and the alkali metal salts thereof wherein n is an integer from zero to 3 and X is a member selected from the group consisting of hydrogen and halo.

17. A compound selected from the group consisting of 1-(2-hydroxy-3-anilinopropyl)-imidazole having the formula:

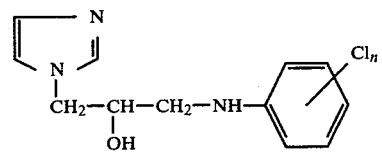

and the alkali metal salts thereof wherein n is an integer from zero to 3.

18. 1-[3-(2,4-dichloroanilino)-2-hydroxypropyl]-imidazole.

19. 1-[3-(3,4-dichloroanilino)-2-hydroxypropyl]-imidazole.

20. 1-(3-anilino-2-hydroxypropyl)-imidazole.

21. 1-[3-(4-chloroanilino)-2-hydroxypropyl]-imidazole.

22. 1-[3-(2,4,5-trichloroanilino)-2-hydroxypropyl]-imidazole.

* * * * *